United States Patent
Hughes et al.

(10) Patent No.: US 7,592,164 B2
(45) Date of Patent: Sep. 22, 2009

(54) PROCESS FOR PREPARING UNSATURATED AMIDES AND CARBOXYLIC ACIDS

(75) Inventors: Jonathan Hughes, Huddersfield (GB); Yvonne Armitage, Holmfirth (GB)

(73) Assignee: Ciba Specialty Chemicals Water Treatments Ltd., West Yorkshire, Bradford (GB)

( * ) Notice: Subject to any disclaimer, the term of this patent is extended or adjusted under 35 U.S.C. 154(b) by 243 days.

(21) Appl. No.: 10/580,445

(22) PCT Filed: Nov. 22, 2004

(86) PCT No.: PCT/EP2004/013251

§ 371 (c)(1),
(2), (4) Date: May 23, 2006

(87) PCT Pub. No.: WO2005/054455

PCT Pub. Date: Jun. 16, 2005

(65) Prior Publication Data

US 2007/0184535 A1    Aug. 9, 2007

(30) Foreign Application Priority Data

Dec. 2, 2003    (GB) ................................. 0327900.7

(51) Int. Cl.
*C12P 13/02* (2006.01)
*C12P 1/02* (2006.01)
*C12N 1/20* (2006.01)

(52) U.S. Cl. .................... 435/129; 435/170; 435/252.1; 435/822

(58) Field of Classification Search ........................ None
See application file for complete search history.

(56) References Cited

U.S. PATENT DOCUMENTS 5,089,411 A    2/1992  Yamada et al. .............. 435/244
6,361,981 B1  3/2002  Symes et al. ................. 435/135
6,562,603 B2  5/2003  Bramucci et al. ........... 435/146
6,916,638 B2  7/2005  Aoki et al. ................... 435/106

FOREIGN PATENT DOCUMENTS

| EP | 0 307 926 | 1/1993 |
| EP | 0 362 829 | 7/1995 |
| EP | 1 055 724 | 11/2000 |
| EP | 1 243 657 | 9/2002 |
| WO | 97/21827 | 6/1997 |
| WO | 01/48234 | 7/2001 |
| WO | 02/12530 | 2/2002 |

OTHER PUBLICATIONS

Watanabe et al., Japan Soc. For bioscience, biotechnology and Agrochem. vol. 51, No. 12, (1987), pp. 3193-3199.
Duckworth et al., Extremophiles, vol. 2, No. 3, Aug. 1998, pp. 359-366.
Bunch, Alan; Antonie Van Leeuwenhoek, vol. 74, No. 103, Jul. 1998, pp. 95 & 96.
Webster et al., Biotechnology Letters, KEW, Surrey, GB, vol. 23, (2001) pp. 95-101.
E. Hann et al., Adv. Synth. Cata. (2003), 345, pp. 775-782.
H. Yamada et al., Biosci. Biotech, Biochem. vol. 60 (9), pp. 1391-1400 (1996).
M. Nawaz et al., Arch Microbiol (1991) 156: pp. 231-238n.
Y. Takashima et al., Journal of Industrial Microbiology & Biotechnology (1998) vol. 20, pp. 220-226.
C. Ramakrishna et al., Biotechnology Letters, vol. 15, No. 3, (Mar. 1993) pp. 267-270.
T. Nagasawa et al. Appl Microbiol biotechnol (1990) 34: pp. 322-324.
F. Rainey et al., International Journal of Systematic Bacteriology, vol. 45, No. 1 (Jan. 1995) pp. 32-36.
T. Leonova et al., Applied Biochemistry and Biotechnology vol. 88, (2000) pp. 231-235.
T. Nagasawa et al. Pure & Appl. Chem. vol. 67, No. 7, (1995)pp. 1241- 1256.

*Primary Examiner*—Vera Afremova
(74) *Attorney, Agent, or Firm*—Shiela A. Loggins

(57) ABSTRACT

A process of producing an amide from a nitrile by the action of a nitrile hydratase enzyme or ammonium salt of an ethylenically unsaturated carboxylic acid from an amide by the action of amidase respectively in which enzymes are obtainable from a microorganism of the *Dietzia* genus.

4 Claims, No Drawings

PROCESS FOR PREPARING UNSATURATED AMIDES AND CARBOXYLIC ACIDS

This application is 371 of PCT/EP04/13251 filed on Nov. 22, 2004, which claims the benefit of United Kingdom application 0327900.7 filed on Dec. 2, 2003.

FIELD OF THE INVENTION

The present invention relates to processes for preparing ethylenically unsaturated carboxylic acids from the corresponding amides employing amidase and for preparing ethylenically unsaturated amides from the corresponding nitrites employing nitrile hydratase. The invention also concerns new nitrile hydratase, amidase and nitrilase enzymes and microorganisms that can produce such enzymes.

BACKGROUND

The enzymic catalysis of chemical reactions is well-documented in the literature. It is well known to employ biocatalysts, such as microorganisms that contain enzymes, for conducting chemical reactions, or to use enzymes that are free of microorganisms. It is known that various ethylenically unsaturated monomers can be prepared by converting a substrate starting material into the desired monomer by use of a biocatalyst.

Nitrile hydratase enzymes are known to catalyse the hydration of nitrites to the corresponding amides. Typically nitrile hydratase enzymes can be synthesized by a variety of microorganisms, for instance microorganisms of the genus *Bacillus, Bacteridium, Micrococcus, Brevibacterium, Corynebacterium, Pseudomonas, Acinetobacter, Xanthobacter, Streptomyces, Rhizobium, Klebsiella, Enterobacter, Erwinia, Aeromonas, Citrobacter, Achromobacter, Agrobacterium, Pseudonocardia, Rhodococcus* and *Comamonas*.

It is known to produce acrylamide from acrylonitrile using as a catalyst nitrile hydratase. When producing these products biologically it is desirable to employ an enzyme which is capable of producing aqueous solutions of acrylamide in high concentration and yet is not poisoned by acrylonitrile and high concentrations of acrylamide.

A review paper by Yamada and Kobayashi, Biosci. Biotech. Biochem 60: 1391-1400 (1996) charts the development of the biocatalysed process for the production of acrylamide monomer up to a concentration of 50%. This review describes the three generations of catalyst developed for the industrial production of acrylamide culminating with *Rhodococcus rhodochrous* J1, a bacterium that requires cobalt as part of the nitrile hydratase enzyme which catalyses the formation of acrylamide from acrylonitrile. The nitrile hydratase is synthesised in very high levels in the bacterium due to the presence of urea as an inducer in the culture medium.

A paper by Nawaz et al., Arch. Microbiol. 156:231-238 (1991), entitled 'Metabolism of acrylonitrile by *Klebsiella pneumoniae*' describes the isolation and growth of the bacterium *K. pneumoniae* and its subsequent rapid utilisation of acrylonitrile and formation of acrylamide which was then further hydrolysed to acrylic acid. The organism was isolated using an enrichment culture technique with acrylonitrile as the sole nitrogen source at pH 7.5.

Takashima et al., J. Indust. Microbiol. Biotechnol. (1998), Nitrile hydratase from a thermophilic *Bacillus smithii*, describes the characteristics of a thermophilic bacterium which synthesises nitrile hydratase. The nitrile hydratase has high acrylonitrile converting activity and the highest activity was at pH 10.5 or above. This would suggest for optimum activity to be achieved for this enzyme, the reaction solution would have to be buffered at this high pH.

Ramakrishna and Desai Biotechnol. Lett. 15: (3) 267-270 (1993) describes the superiority of cobalt induced acrylonitrile hydratase of *Arthrobacter* sp. IPCB-3 for conversion of acrylonitrile to acrylamide compared with an iron containing nitrile hydratase in this organism. This bacterium requires cobalt, and urea as a co-factor and inducer respectively to give the highest nitrile hydratase activity. Although the cobalt containing nitrile hydratase of this organism appears to have good acrylonitrile tolerance, at acrylamide concentrations of greater than 25% the enzyme activity was greatly reduced.

Various strains of the *Rhodococcus rhodochrous* species have been found to very effectively produce nitrile hydratase enzyme. EP-0 307 926 describes the culturing of *Rhodococcus rhodochrous*, specifically strain J1 in a culture medium that contains cobalt ions. The nitrile hydratase can be used to hydrate nitriles into amides, and in particular the conversion of 3-cyanopyridine to nicotinamide. This organism is further described in EP-0362829, which describes a method for cultivating bacteria of the species *Rhodococcus rhodochrous* comprising at least one of urea and cobalt ion for preparing the cells of *Rhodococcus rhodochrous* having nitrile hydratase activity. Specifically described is *Rhodococcus rhodochrous* J1.

*Rhodococcus rhodochrous* J1, is used commercially to manufacture acrylamide monomer from acrylonitrile and this process has been described by Nagasawa and Yamada, Pure Appl. Chem. 67: 1241-1256 (1995).

Leonova et al., Appl. Biochem. Biotechnol. 88: 231-241 (2000) entitled, "Nitrile Hydratase of *Rhodococcus*", describes the growth and synthesis of nitrile hydratase in *Rhodococcus rhodochrous* M8. The nitrile hydratase of this strain is induced by the presence of urea in the medium, which is also used as a nitrogen source for growth by this organism. Cobalt is also required for high nitrile hydratase activity. This literature paper mainly looks at induction and metabolic effects.

Each of the aforementioned references describe bacteria that produce nitrile hydratase enzymes. All of these disclosures require that the bacteria are grown at approximately neutral pH.

The genus *Dietzia* was first described by Rainey et al., Int. J. Syst. Bacteriol 45: 32-36 (1995). *Dietzia maris* became the type species for the genus. In 1999 a further species addition was made: *Dietzia natronolimnaea*, this species first being described by Grant et al., Extremophiles 2: 359-366 (1998) in the publication entitled '*Dietzia natronolimnaios* sp. Nov., a new member of the genus *Dietzia* isolated from an East African soda lake'.

The *Dietzia natronolimnalos* strain isolated by these researchers 15LN1 (CBS 107.95) is an alkaliphile and as such grows at high pH (10) and in addition it grows in culture media containing high salt concentrations (40 g/l).

The *Dietzia* genus has been described for the catalysis of the synthesis of saturated compounds. For instance, WO-A-02/12530 describes a process for preparing 3-hydroxycarboxylic acid by the hydrolysis of 3-hydroxynitrile using *Dietzia* sp. ADL1 (ATCC PTA-1854).

A process for the preparation of glycine from glycinonitrile using microorgansims is described in WO01/048234. A number of microbial species are described in this patent including *Dietzia maris*.

Microorganisms which specifically produce acrylonitrile hydratase enzymes or other analogous enzymes for converting unsaturated nitriles to the corresponding amides or carboxylic acids, are grown at about neutral pH, that is approximately pH 6 to 8. Consequently, it can be more difficult to maintain the sterility during the culturing of the bacterium as it is recognized that many, many microorganisms will grow at this pH. A particular problem that can occur therefore, is that the fermentation can become contaminated with other microorganisms. Such contamination not only impairs the production of the required enzyme, but may also result in undesirable by-products when used to convert the unsaturated nitrile to the desired product. Additionally, it is most undesirable to have other microorganisms present since in order to ensure they are not harmful, that is not pathogenic, the unknown contaminants would have to be identified. Consequently, the fermentation would have to be abandoned which is both expensive and time-consuming.

It has already been described that urea is often added to the fermentation medium as an inducer of the nitrile hydratase of many organisms that are shown to produce acrylamide from acrylonitrile. Solutions of urea can be alkaline due to the presence of ammonium ion in the solution. And additionally if the urea is degraded at all during the fermentation this releases ammonium ion causing the pH of the medium to increase, unless buffering capacity in the form of buffer salts is added at high levels, or more likely the increasing pH effects are counteracted by the use of acid addition to the fermentation. This is therefore a further problem with fermenting the microorganism at neutral pH in that it is normally required to buffer the reaction mixture in order to counteract the effect of adding urea. Buffer solutions that are used may include phosphate salts, citric acid in combination with a basic salt such as phosphate, tris or any other buffer generally known to be applicable to use in fermentation systems to give rise to a neutral pH. Acids that may be used for buffering purposes include phosphoric, acetic, sulphuric and any other that may be suitable for this purpose.

Nitrile

A further problem is that many microorganisms tend not to be tolerant to high salt concentrations and this can result in cell leakage during growth and during use of the bacteria as a biocatalyst due to the differences in the osmotic pressure within the cell and in the fermentation or reaction medium. For instance if a microorganism is being used to prepare a carboxylic acid salt, this solution would have a higher ionic strength than water or buffer solution. It might be the case that depending upon the microorganism used, the difference in the osmotic pressure in the cell and the reaction solution would cause the cell to rupture thus reducing the capability of the organism to act as an effective biocatalyst and also by virtue of the intracellular material now being present as a contaminant of the reaction mixture, which may be wholly undesirable.

SUMMARY OF THE INVENTION

It would therefore be desirable to provide a process and a biocatalyst in the form of a microorganism which overcomes all of these problems. In particular it will be desirable to provide a process in which ethylenically unsaturated carboxylic acids and their ammonium salts can be prepared from the corresponding amide and in which ethylenically unsaturated amides are prepared from the corresponding nitrile in high yield and without the risk of unwanted byproducts.

In accordance with the first aspect of the present invention we provide a process of producing an ethylenically unsaturated amide, wherein a nitrile is treated with an enzyme which is a nitrile hydratase in an aqueous medium, characterised in that the nitrile hydratase is obtainable from a microorganism of the *Dietzia* genus.

According to the second aspect of the present invention we provide a process of producing an ammonium salt of an ethylenically unsaturated carboxylic acid, wherein an amide is treated with an enzyme which is an amidase in an aqueous medium, characterised in that the amidase is obtainable from a microorganism of the *Dietzia* genus.

Unexpectedly we have found that microorganisms of the *Dietzia* genus are capable of producing specific nitrile hydratase and amidase enzymes suitable for converting ethylenically unsaturated nitriles to the corresponding amides and carboxylic acids on an industrial scale.

The *Dietzia* microorganisms can be cultured at alkaline pHs, for instance pH 9 to 10 which facilitates improved sterility of the fermentation. Advantageously we now find that the fermentation and bio-process can be integrated and thus carried out in a single step.

Furthermore, the *Dietzia* microorganisms have unexpectedly been found to exhibit high tolerance to high concentrations of unsaturated carboxylic acids and therefore enable ethylenically unsaturated amides, such as acrylamide, to be converted into the carboxylic acid, such as acrylic acid (as the ammonium salt) at high concentrations. Typically such high concentrations of acids could be expected to bring about cell leakage and render them unsuitable for re-use in a bioconversion process. It is also possible to use the *Dietzia* microorganisms and nitrile hydratase produced therefrom to produce acrylamide in high concentrations. In a further development of the process ethylenically unsaturated carboxylic acids can be prepared from the corresponding nitrile in a two-step process involving a first stage hydration to the corresponding amide using the nitrile hydratase of *Dietzia* and a second stage conversion of the amide into the carboxylic acid using the amidase produced by *Dietzia*.

DETAILED DESCRIPTION OF THE INVENTION

Preferably the ethylenically unsaturated nitrile is (meth) acrylonitrile, the ethylenically unsaturated amide is (meth) acrylamide and the ethylenically unsaturated carboxylic acid is (meth) acrylic acid.

In each case the enzymes may be extracted from the microorganism and used directly in the reaction. Preferably though the enzymes are comprised within whole cells of the microorganism.

The microorganism may be any species of the *Dietzia* genus but is preferably a species of *Dietzia* selected from the group consisting of *Dietzia natronolimnaios*, *Dietzia maris* and *Dietzia psychralcaliphila*.

Most preferably the microorganism used to provide the nitrile hydratase or amidase enzymes is a new microorganism *Dietzia natronolimnaios* strain NCIMB 41165. In a further aspect of the present invention we claim the new microorganism *Dietzia natronolimnaios* strain NCIMB 41165.

The nitrile hydratase enzyme and the amidase enzyme each obtainable by culturing *Dietzia natronolimnaios* strain NCIMB 41165 are also new. The details of strain NCIMB 41165 are given below:

1. Origin and Deposition

The strain was isolated by us from soil in Bradford, England and deposited on Mar. 5, 2003 at the National Collection of Industrial and Marine Bacteria (NCIMB), where it was assigned the accession number NCIMB 41165 under the Budapest Treaty.

NCIMB Ltd.
Ferguson Building
Crabstone Estate
Bucksburn, Aberdeen
Scotland, AB219YA 2. Morphological and Cultural Characteristics
  (1) Polymorphic growth
  (2) Motility: immotile
  (3) Non-spore former
  (4) Gram positive
  (5) Aerobic
  (6) Growth on nutrient agar gives pink round shiny colonies within 48 hours at 30° C.
  (7) Growth on Alkaline Medium yields bright red shiny colonies with mucous texture.

3. Cultivation and Nitrile Hydratase Synthesis

The *Dietzia* bacteria, for instance *Dietzia natronolimnalos*, of the present invention can be cultivated under any conditions suitable for the purpose, but it is most preferable to grow in a medium that is alkaline and which may also contain salt at high levels. Examples of suitable culture media are shown in the patent examples.

In addition a suitable inducer for the nitrile hydratase or amidase should be included in the growth medium. These could be a nitrile such as acetonitrile, propionitrile, isobutyronitrile or acrylonitrile or an amide such as acetamide, propionamide, isobutyramide or acrylamide. Specifically for nitrile hydratase activity for amide formation, urea could be used as enzyme inducer.

The following examples illustrate the invention.

EXAMPLE 1

A) *Dietzia natronolimnaios* NCIMB 41165 was isolated from soil and it was grown in a 2 L baffled Erlenmeyer flask containing 400 mL culture medium containing the following constituents (g/L): diPotassium hydrogen phosphate 0.7; Potassium hydrogen phosphate 0.3; glucose 10.0; yeast extract 3.0; peptone 5.0; magnesium sulphate heptahydrate 0.5; Urea 5.0; cobalt chloride hexahydrate 0.01; tap water to 1 L. The pH of the medium was adjusted to pH 7.2. The culture was grown at 28° C. for 5 days. Biomass was harvested by centrifugation and stored at −20° C.

B) *Dietzia natronolimnaios* NCIMB 41165 was grown as described in (A). However the urea was removed from the medium and acetonitrile was added at 5 g/L.

C) *Dietzia natronolimnaios* NCIMB 41165 was grown as described in (A). However the urea was removed from the medium and isobutyronitrile was added at 5 g/L D) A portion of the biomass from (A) was defrosted and suspended in 50 mM pH 7 sodium phosphate buffer (20 mL). The suspension was incubated at 15° C. for 10 minutes. Acrylonitrile (0.247 mL) was added to the cell suspension and the mixture was shaken. A sample (0.3 mL) was removed immediately and it was added to a solution of 8.8% o-phosphoric acid (0.3 mL). The cells were removed by centrifugation. The supernatant was analysed by HPLC for the presence of acrylonitrile, acrylamide and ammonium acrylate. The reaction was carried out for 10 minutes. The specific nitrile hydratase activity of the cells was 44, 170 μmoles/minute/g dry weight of cells.

A portion of the biomass from (B) was treated as described in (D). The specific nitrile hydratase activity of the cells was 11,060 μmoles/minute/g dry weight of cells.

E) A portion of the biomass from (C) was treated as described in (D). The specific nitrile hydratase activity of the cells was 1150 μmoles/minute/g dry weight of cells.

EXAMPLE 2

A) *Dietzia natronolimnaios* NCIMB 41165 is grown for 4 days at 28° C. in the following culture medium in g/L: diPotassium hydrogen phosphate 0.7; Potassium hydrogen phosphate 0.3; peptone 5.0; yeast extract 5.0; glucose 10; urea, 5.0; magnesium sulphate heptahydrate, 0.5; cobalt chloride, 0.01. The pH of the medium is adjusted to 7.2.

B) A portion of harvested cells is resuspended in 50 mM pH 7.0 sodium phosphate buffer solution. Approximately 1% acrylonitrile (w/w) is added to the cell suspension,. which is then incubated at 15° C. for 20 minutes. After 20 minutes the acrylonitrile is converted to 0.79% acrylamide and 0.57% ammonium acrylate.

The invention claimed is:

1. A process of producing an ethylenically unsaturated amide, wherein a nitrile is treated with an enzyme which is a nitrile hydratase in an aqueous medium, characterised in that the nitrile hydratase is obtained from a microorganism of a species of *Dietzia* genus, which nitrile hydratase is comprised within whole cells of the microorganism, and which microorganism is *Dietzia natronolimnaios* strain NCIMB 41165.

2. A process according to claim 1 in which the ethylenically unsaturated nitrile is (meth) acrylonitrile.

3. A process according to claim 1 in which the ethylenically unsaturated amide is (meth) acrylamide.

4. An isolated *Dietzia natronolimnaios* strain NCIMB 41165.

* * * * *

UNITED STATES PATENT AND TRADEMARK OFFICE
CERTIFICATE OF CORRECTION

PATENT NO.       : 7,592,164 B2                                                      Page 1 of 1
APPLICATION NO.  : 10/580445
DATED            : September 22, 2009
INVENTOR(S)      : Hughes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 355 days.

Signed and Sealed this

Twenty-first Day of September, 2010

David J. Kappos
*Director of the United States Patent and Trademark Office*